(12) United States Patent
Kataoka et al.

(10) Patent No.: US 8,774,356 B2
(45) Date of Patent: Jul. 8, 2014

(54) WAVELENGTH DISPERSIVE X-RAY FLUORESCENCE SPECTROMETER

(75) Inventors: Yoshiyuki Kataoka, Takatsuki (JP); Hisashi Inoue, Takatsuki (JP); Kosuke Kawakyu, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 0 days.

(21) Appl. No.: 13/997,839

(22) PCT Filed: Apr. 3, 2012

(86) PCT No.: PCT/JP2012/059080
§ 371 (c)(1), (2), (4) Date: Jun. 25, 2013

(87) PCT Pub. No.: WO2012/160881
PCT Pub. Date: Nov. 29, 2012

(65) Prior Publication Data
US 2013/0294577 A1 Nov. 7, 2013

(30) Foreign Application Priority Data

May 20, 2011 (JP) .................................. 2011-113735

(51) Int. Cl.
*G01N 23/223* (2006.01)
*G01D 18/00* (2006.01)

(52) U.S. Cl.
USPC ............................. 378/45; 378/44; 378/207

(58) Field of Classification Search
USPC ............... 378/44, 45, 46, 47, 48, 49, 50, 207
See application file for complete search history.

(56) References Cited

U.S. PATENT DOCUMENTS

| | | | |
|---|---|---|---|
| 3,732,422 A | 5/1973 | Brunson et al. | |
| 4,253,154 A | 2/1981 | Russ et al. | |
| 4,922,442 A | 5/1990 | Bolk et al. | |
| 5,684,850 A * | 11/1997 | Warburton et al. | 378/53 |
| 6,392,236 B1 * | 5/2002 | Maekawa et al. | 250/369 |
| 6,404,847 B1 | 6/2002 | Ueki et al. | |
| 6,584,413 B1 * | 6/2003 | Keenan et al. | 702/28 |
| 6,590,957 B1 * | 7/2003 | Grudberg et al. | 378/91 |

(Continued)

FOREIGN PATENT DOCUMENTS

| | | |
|---|---|---|
| CN | 1056582 A | 11/1991 |
| CN | 101416047 A | 4/2009 |

(Continued)

OTHER PUBLICATIONS

B. D. D Cullity and S. R. Stock, Elements of X-Ray Diffraction (Upper Saddle River, NJ: Prentice Hall, third edition, 2001), pp. 198-215.*

(Continued)

*Primary Examiner* — Allen C. Ho
(74) *Attorney, Agent, or Firm* — Sughrue Mion, PLLC

(57) ABSTRACT

In the wavelength dispersive X-ray fluorescence spectrometer of the present invention, a counting loss correcting unit (11), when correcting a counting rate of pulses determined by a counting unit (10) on the basis of a dead time of a detector (7), stores beforehand a correlation between a predetermined pulse height range, within which pulses are selected by a pulse height analyzer (9), and the dead time and determines the dead time so as to correspond to the predetermined pulse height range during a measurement on the basis of the stored correlation.

4 Claims, 3 Drawing Sheets

(56) References Cited

U.S. PATENT DOCUMENTS

| | | | |
|---|---|---|---|
| 6,609,075 B1* | 8/2003 | Warburton et al. | 702/87 |
| 6,668,038 B2* | 12/2003 | Kataoka et al. | 378/45 |
| 6,675,106 B1* | 1/2004 | Keenan et al. | 702/28 |
| 7,197,523 B2* | 3/2007 | Lutkenhaus et al. | 708/255 |
| 7,342,997 B2 | 3/2008 | Ueda et al. | |
| 7,430,481 B2* | 9/2008 | Mott | 702/40 |
| 7,741,609 B2* | 6/2010 | Mott | 250/370.09 |
| 7,949,093 B2 | 5/2011 | Kataoka et al. | |
| 7,966,155 B2* | 6/2011 | Warburton et al. | 702/190 |
| 8,258,480 B2* | 9/2012 | Olcott et al. | 250/363.02 |
| 8,450,695 B2* | 5/2013 | Kappler et al. | 250/370.09 |
| 2006/0285642 A1 | 12/2006 | Ueda et al. | |
| 2009/0116613 A1 | 5/2009 | Kataoka et al. | |

FOREIGN PATENT DOCUMENTS

| | | | |
|---|---|---|---|
| JP | 49-65270 A | 6/1974 | |
| JP | 49-75189 A | 7/1974 | |
| JP | 53-40574 A | 4/1978 | |
| JP | 53-70482 A | 6/1978 | |
| JP | 55-83863 A | 6/1980 | |
| JP | 55-95855 A | 7/1980 | |
| JP | 61-175555 A | 8/1986 | |
| JP | 2-226058 A | 9/1990 | |
| JP | 07306267 A | 11/1995 | |
| JP | 9-211138 A | 8/1997 | |
| JP | 2001337168 A | 12/2001 | |
| JP | 2006-322885 A | 11/2006 | |
| JP | 2008-191044 A | 8/2008 | |

OTHER PUBLICATIONS

Nicholas Tsoulfanidis, Measurement and Detection of Radiation (Washington, DC: Taylor & Francis, second edition, 1995), pp. 17-21, 74-76, 307-313, 344-349.*

Decision of Grant of JP 2011-113735 dated Aug. 21, 2012.

Notification of Reason for Rejection of JP 2011-113735 dated May 1, 2012.

English translation of INternational Preliminary Report on Patentability mailed Nov. 28, 2013 for PCT/JP2012/059080.

Office Action, dated Mar. 27, 2014, issued by the Chinese Patent Office in corresponding Chinese patent application No. 201280010736.6.

* cited by examiner

WAVELENGTH DISPERSIVE X-RAY FLUORESCENCE SPECTROMETER

CROSS REFERENCE TO RELATED APPLICATIONS

This application is a National Stage of International Application No. PCT/JP2012/059080 filed Apr. 3, 2012, claiming priority based on Japanese Patent Application No. 2011-113735 filed May 20, 2011, the contents of all of which are incorporated herein by reference in their entirety.

BACKGROUND OF THE INVENTION

1. Field of the Invention

The present invention relates to a wavelength dispersive X-ray fluorescence spectrometer.

2. Description of Related Art

In the fluorescent X-ray analysis of a wavelength dispersive method, a sample is irradiated with primary X-rays, fluorescent X-rays emitted from the sample are then monochromated by a spectroscopic device and the monochromated fluorescent X-rays are subsequently detected by a detector (such as, for example, a scintillation counter or a gas flow proportional counter to generate pulses. The voltage of those pulses, that is, the pulse height depends on the energy of the fluorescent X-rays and the number of pulses per unit time depends on the intensity of the fluorescent X-rays. In view of this, by selecting pulses of a pulse height within a predetermined pulse height range from those pulses with the use of a pulse height analyzer, a counting rate thereof (the number of pulses per unit time) has been determined by a counting unit (a counting circuit) such as, for example, a scaler or the like.

When one pulse is generated upon incidence of X-ray photon on the detector, no pulse is generated for a defined period of time subsequent thereto, that is, a so-called dead time, even though X-ray photons are incident on the detector. Also, if the counting rate becomes high, pulses become overlapped within the counting unit. In view of those, a counting loss of the pulses to be counted tends to occur.

Accordingly, it is a conventional practice that as regards to both of the counting loss resulting from the detector and that in the counting unit, with respect to the specific pulse height range the dead time $\tau$ is determined for each detector as one value and, using this dead time $\tau$, by means of, for example, the following equation (1), the counting rate (counting intensity) Nm of the pulses determined by the counting unit is corrected, followed by determination of a counting loss corrected counting rate, that is, a counting loss correction intensity Nt. In this respect, see, for example, the patent documents 1 and 2 listed below.

$$Nt = Nm/(1-\tau Nm) \quad (1)$$

Also, an equation in which the counting rate different from the equation (1) above is used so as to avoid effects brought about by higher order reflection lines of inter-elements (See, for example, the patent document 1 listed below.), an equation in which a denominator of the equation (1) above is rendered to be an equation of higher degree with respect to Nm, different values of coefficients are employed and the equation thereof converted into a table (See, for example, the patent document 2 listed below.) have been suggested. According to those equations and tables for the counting loss correction, which are employed in the conventional art, even though the predetermined pulse height range, within which pulses are selected by the pulse height analyzer, is changed depending on a measurement, the counting loss correction intensity is determined while the coefficients of $Nm^n$ remain the same regardless of the change of the predetermined pulse height range.

PRIOR ART LITERATURE

[Patent Document 1] JP Laid-open Patent Publication No. H02-226058

[Patent Document 2] JP Laid-open Patent Publication No. S61-175555

It has, however, been found that in reality the dead time changes with the predetermined pulse height range within which pulses are selected by the pulse height analyzer, that is, preset values for the lower and upper limits of the pulse height analyzer and, accordingly, if a fixed value is chosen for the particular pulse height range, the counting rate of the pulses determined by the counting unit cannot be accurately corrected when the predetermined pulse height range during the measurement is changed.

SUMMARY OF THE INVENTION

In view of the foregoing, the present invention has been devised to substantially eliminate the above discussed problems and inconveniences inherent in the prior art and is intended to provide a wavelength dispersive X-ray fluorescence spectrometer of a type capable of accurately correcting the counting rate of pulses, determined by the counting unit, even though the predetermined pulse height range, within which pulses are selected by the pulse height analyzer, is changed.

In order to accomplish the foregoing objective, the present invention in accordance with a first aspect thereof provides a wavelength dispersive X-ray fluorescence spectrometer, which includes an X-ray source for irradiating a sample with primary X-rays; a spectroscopic device for monochromating fluorescent X-rays emitted from the sample; a detector for receiving the fluorescent X-rays, which have been monochromated by the spectroscopic device, and generating pulses with a pulse height proportional to the energy of the fluorescent X-rays in a number dependent on the intensity of the fluorescent X-rays; a pulse height analyzer for selecting pulses with a pulse height within a predetermined pulse height range from the pulses generated by the detector; a counting unit for determining the counting rate of the pulses selected by the pulse height analyzer; and a counting loss correcting unit for correcting the counting rate of the pulses, determined by the counting unit on the basis of a dead time of the detector, with respect to a counting loss of the pulses to be counted. The counting loss correcting unit referred to above stores beforehand a correlation between the predetermined pulse height range and the dead time and is operable to determine the dead time, which corresponds to the predetermined pulse height range during a measurement, on the basis of the correlation so stored.

According to the wavelength dispersive X-ray fluorescence spectrometer designed in accordance with the first aspect of the present invention, since the counting loss correcting unit stores therein the correlation between the predetermined pulse height range and the dead time and is operable to determine the dead time, which corresponds to the predetermined pulse height range during the measurement, on the basis of the correlation so stored, the counting rate of the pulses determined by the counting unit can be accurately corrected even though the predetermined pulse height range within which pulses are selected by the pulse height analyzer, that is, the predetermined pulse height range set in the pulse height analyzer is changed.

In the wavelength dispersive X-ray fluorescence spectrometer designed in accordance with the first aspect of the present invention, the counting loss correcting unit preferably stores beforehand a correlation between the predetermined pulse height range and the dead time in a standard spectrometer to be used as a basis, which is of the same kind as such wavelength dispersive X-ray fluorescence spectrometer, and a ratio between the dead time in such wavelength dispersive X-ray fluorescence spectrometer and the dead time in the standard spectrometer for a predetermined pulse height range to be used as a basis and preferably determines the dead time, which corresponds to the predetermined pulse height range during the measurement, on the basis of the correlation and the ratio so stored. In this case, there is no need to determine beforehand the correlation between the predetermined pulse height range and the dead time in such spectrometer and the correlation between the predetermined pulse height range and the dead time, determined in the standard spectrometer which is of the same kind as such spectrometer, can be utilized.

The wavelength dispersive X-ray fluorescence spectrometer according to the second aspect of the present invention includes an X-ray source for irradiating a sample with primary X-rays; a spectroscopic device for monochromating fluorescent X-rays emitted from the sample; a detector for receiving the fluorescent X-rays, which have been monochromated by the spectroscopic device, and generating pulses of a pulse height proportional to an energy of the fluorescent X-rays in a number dependent on an intensity of the fluorescent X-rays; a pulse height analyzer for selecting pulses of a pulse height within a predetermined pulse height range from the pulses generated by the detector; a counting unit for determining a counting rate of the pulses selected by the pulse height analyzer; and a counting loss correcting unit for correcting the counting rate of the pulses, determined by the counting unit, on the basis of a dead time of the detector with respect to a counting loss of the pulses to be counted. In this wavelength dispersive X-ray fluorescence spectrometer, the counting loss correcting unit stores beforehand a plurality of pulse height distributions for their respective counting rates and is operable to determine the dead time, which corresponds to the predetermined pulse height range during a measurement, on the basis of the pulse height distributions so stored.

In the wavelength dispersive X-ray fluorescence spectrometer designed in accordance with the second aspect of the present invention, since the counting loss correcting unit stores therein the plurality of pulse height distributions for their respective counting rates and is operable to determine the dead time, which corresponds to the predetermined pulse height range during the measurement, on the basis of the pulse height distributions so stored, the counting rate of the pulses determined by the counting unit can be accurately corrected even though the predetermined pulse height range set in the pulse height analyzer is changed.

Also, in the wavelength dispersive X-ray fluorescence spectrometer constructed in accordance with the present invention, the counting loss correcting unit referred to above preferably further stores beforehand a proportionality coefficient of an energy resolution of the detector relative to the inverse of the square root of the energy of the fluorescent X-rays and a correlation between the energy resolution of the detector and the dead time and is operable to determine the dead time, which corresponds to the predetermined pulse height range during the measurement, on the basis of the proportionality coefficient and the correlation so stored. In this case, such as observable with a scanning type wavelength dispersive X-ray fluorescence spectrometer, even though not only the predetermined pulse height range set in the pulse height analyzer but also the energy of the fluorescent X-rays incident on the detector is changed, the counting rate determined by the counting unit can be accurately corrected.

BRIEF DESCRIPTION OF THE DRAWINGS

The present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, identical reference numerals are used to denote identical parts throughout the several views, and:

DESCRIPTION OF PREFERRED EMBODIMENTS

Figure 1:
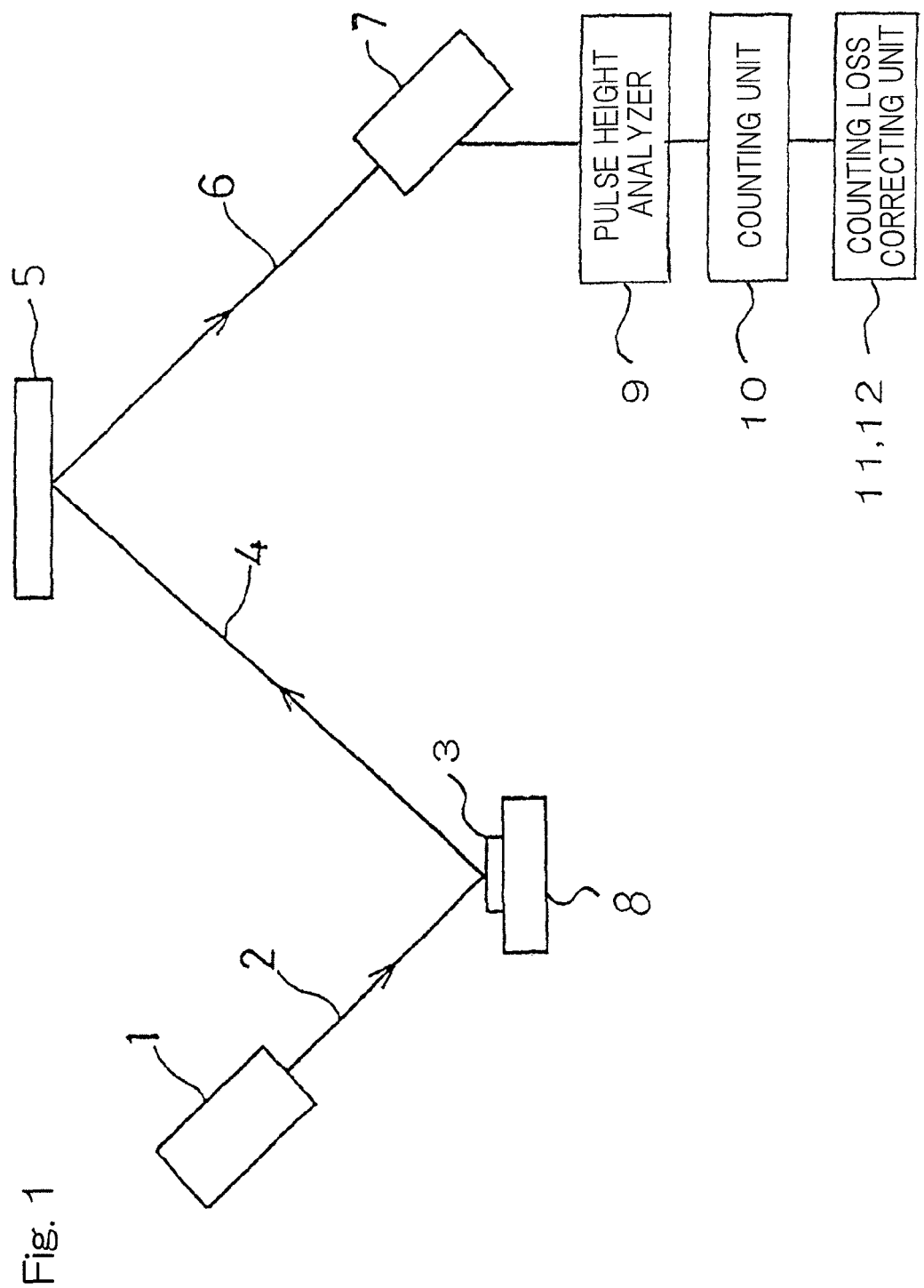
FIG. 1 is a schematic diagram showing a wavelength dispersive X-ray fluorescence spectrometer in accordance with first and second preferred embodiments of the present invention.

Hereinafter, a wavelength dispersive X-ray fluorescence spectrometer in accordance with a first preferred embodiment of the present invention will be described with particular reference to the accompanying drawings. As shown in FIG. 1, this wavelength dispersive X-ray fluorescence spectrometer includes an X-ray source 1 such as, for example, an X-ray tube for irradiating a sample 3 placed on a sample table 8 with primary X-rays 2, a spectroscopic device 5 for monochromating fluorescent X-rays 4 emitted from the sample 3, a detector 7 capable of receiving the fluorescent X-rays 6, which have been monochromated by the spectroscopic device 5, and then generating pulses of a pulse height, which is proportional to the energy of the fluorescent X-rays 6, in a number dependent on an intensity of the fluorescent X-rays, a pulse height analyzer 9 for selecting pulses of a pulse height within a predetermined pulse height range from those pulses generated by the detector 7, a counting unit 10 for determining a counting rate of the pulses selected by the pulse height analyzer 9, and a counting loss correcting unit 11 for correcting the counting rate of the pulses, which has been determined by the counting unit 10 on the basis of a dead time of the detector 7, with respect to a counting loss of the pulses to be counted. And, the counting loss correcting unit 11 stores beforehand a correlation between the predetermined pulse height range and the dead time and determines, on the basis of the correlation stored therein, the dead time so as to correspond to the predetermined pulse height range during a measurement.

Figure 2:
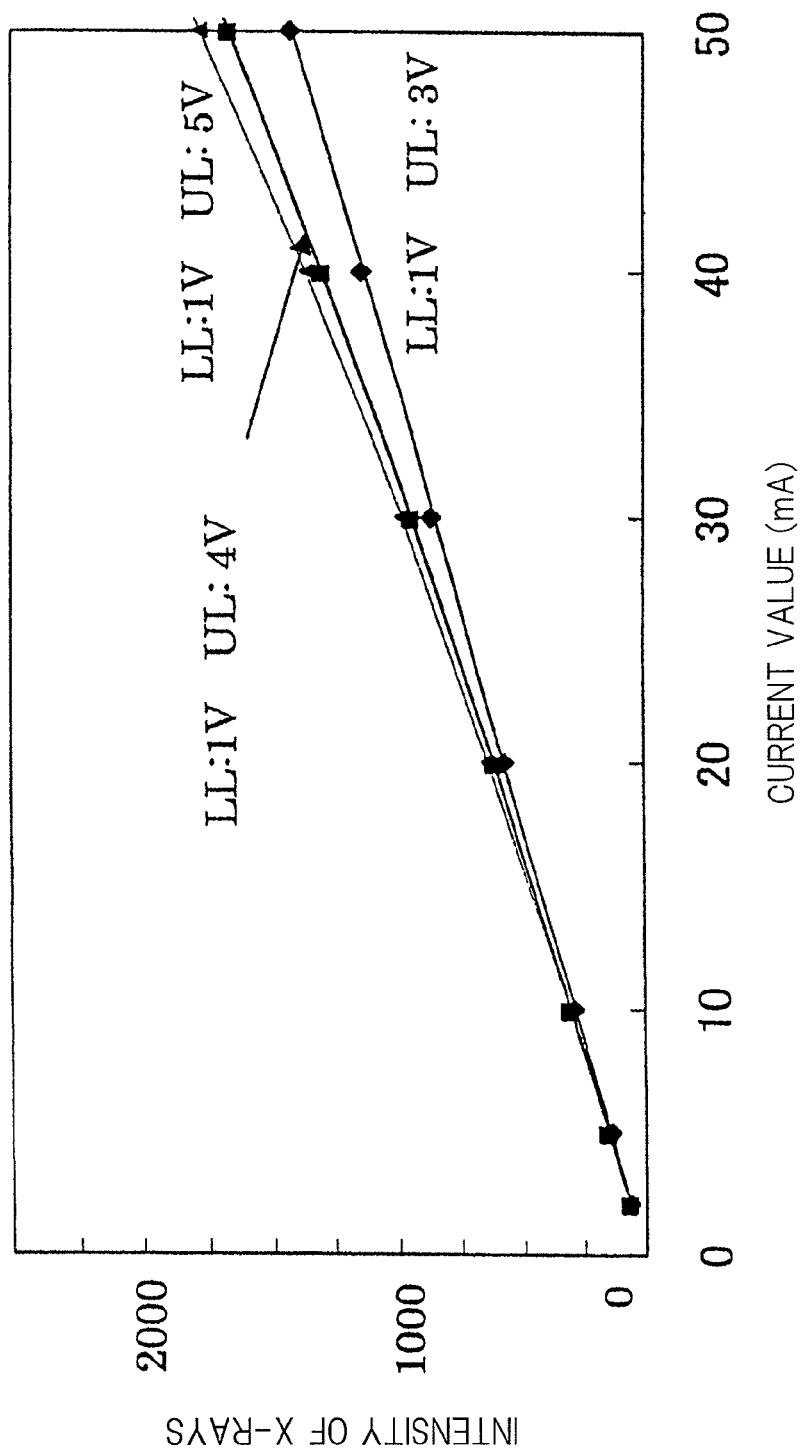
FIG. 2 is a chart showing examples of evaluations on counting linearity exhibited by the conventional wavelength dispersive X-ray fluorescence spectrometer.

A confirmatory experiment that has led to the construction of the counting loss correcting unit 11 will now be discussed. An example in which a counting linearity, exhibited when Cu—Kα line was measured with the use of the conventional wavelength dispersive X-ray fluorescence spectrometer of a type utilizing a scintillation counter as a detector was evaluated, is shown in FIG. 2. The Y-axis represents a counting loss corrected counting rate, that is, a counting loss corrected intensity of X-rays in cps. The X-axis represents a tube current value (mA) applied to the X-ray tube and a tube voltage value (kV) is fixed. In this example, if the peak value of a pulse height distribution is assumed to be 2V, the dead time used in the counting loss correction can be determined for a preset lower limit value LL=1V and a preset upper limit value UL=3V of the detector, that is, for a pulse height range of 1 to 3V. If the counting loss correction is proper, a correction between the current value and the intensity of X-rays exhibits a linearity, but it will readily be seen that the counting loss correction is excessive when the preset upper limit value exceeds 3V such as for UL=4V or UL=5V, for dead time determined at UL=3V.

Figure 3:
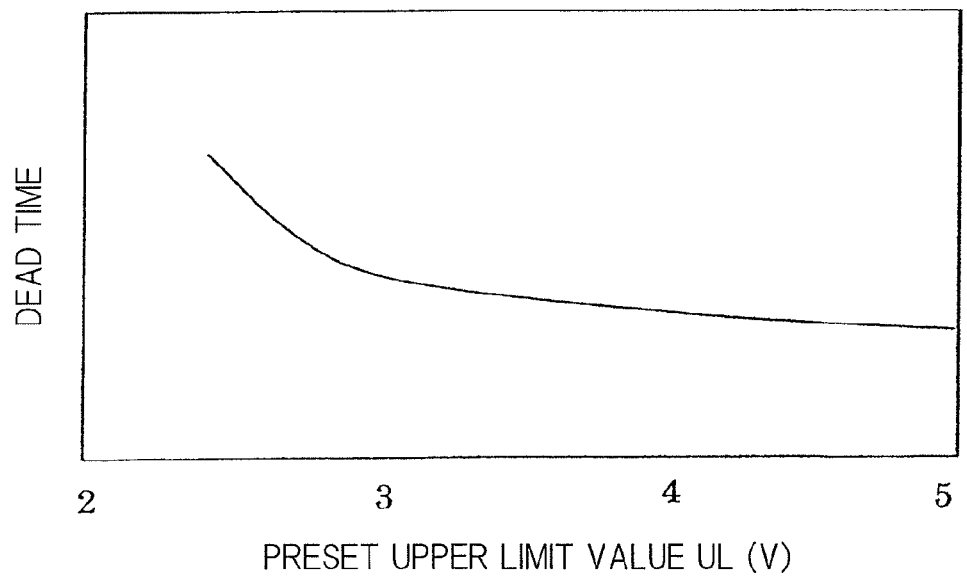
FIG. 3 is a chart showing an example of change of the dead time exhibited when a preset upper limit in the pulse height analyzer is changed.

Also, when the preset lower limit value LL of the pulse height analyzer is fixed to 1V and the present upper limit value thereof UL is changed within a range of 2.5 to 5V, it has been ascertained that the dead time decreases with increase of the preset upper limit value UL as shown in FIG. 3.

In view of the above, arrangement has been made that the correlation between the predetermined pulse height range within which pulses are selected by the pulse height analyzer 9, that is, the predetermined pulse height range set in the pulse height analyzer 9, and the dead time is stored in the counting loss correcting unit 11 beforehand and, based on the stored correlation, the dead time can be determined so as to correspond to the predetermined pulse height range of the measurement condition of the sample to be analyzed (an unknown sample). More specifically, this correlation is a table drawn up by determining the dead time in each of representative combinations of the preset lower and upper limit values of the pulse height analyzer 9, that is, the combinations are frequently used in the art concerned.

This table can be drawn up, for example, in the following manner. At the outset, with the use of a standard sample the measurement is carried out at one of representative predetermined pulse height ranges (which is assumed as a pulse height range A) to determine the counting rate $Nm_{A1}$ at a tube current value of 5 mA and a counting rate $Nm_{A2}$ at a tube current value of 50 mA. Assuming that the counting rate $Nm_{A1}$, when corrected accurately as to its counting loss, becomes a counting rate $Nt_{A1}$, the counting rate $Nm_{A2}$, when similarly accurately corrected as to its counting loss, should become a counting rate $10Nt_{A1}$, and, therefore, from the equation (1) discussed above, the following equations (2) and (3) establish. Provided that a dead time for the pulse height range A is expressed by $\tau_A$.

$$Nt_{A1}=Nm_{A1}/(1-\tau_A Nm_{A1}) \quad (2)$$

$$10Nt_{A1}=Nm_{A2}/(1-\tau_A Nm_{A2}) \quad (3)$$

Since the counting rates $Nm_{A1}$ and $Nm_{A2}$ are known, the dead time $\tau_A$ of the pulse height range A can be calculated from the equations (2) and (3) above. By performing this work for each of the representative predetermined pulse height ranges, the table referred to above can be drawn up.

Also, in the case of a plurality of wavelength dispersive X-ray fluorescence spectrometers that utilizes the same detector and the same counting unit (counting circuit), the absolute value of the dead time may differ somewhat among those spectrometers, but the amount of change in relative value of the dead time among those spectrometers is small. Accordingly, instead of determining the correlation between the predetermined pulse height range and the dead time in such wavelength dispersive X-ray fluorescence spectrometer and then causing it to be stored in the counting loss correcting unit 11, arrangement has been made that while a correlation between the predetermined pulse height range and the dead time, which has already been determined in connection with a standard spectrometer of the same kind, which is used as a basis, as such spectrometer and a ratio between the dead time in such spectrometer and the dead time in the standard spectrometer at the predetermined pulse height range, which range is used as a basis, are stored beforehand, the dead time may be determined so as to correspond to the predetermined pulse height range during the measurement on the basis of the correlation and the ratio so stored.

Figure 4:
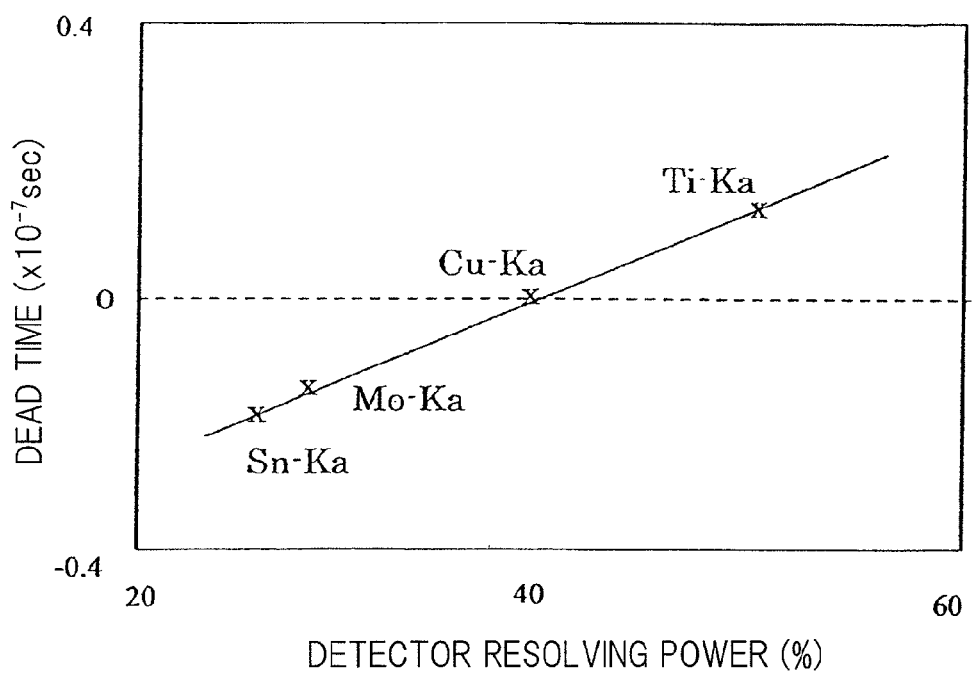
FIG. 4 is a chart showing an example of the correlation between the energy resolution of the detector and the dead time.

Moreover, since the energy of the fluorescent X-rays that is measured affects the dead time, although it does not affect it as much as the preset lower limit value and the preset upper limit value of the pulse height analyzer, a correlation between the energy of the fluorescent X-rays and the dead time has been examined. Considering that the energy resolution of the detector is proportional to the inverse of the square root of the energy of the fluorescent X-rays and that the dead time is in actuality related to the energy resolution of the detector, the correlation between the energy resolution of the detector and the dead time, instead of the correlation between the energy of the fluorescent X-rays and the dead time, was examined by determining the dead time by changing the fluorescent X-rays. The correlation exhibited when the preset lower limit value LL and the preset upper limit value UL of the pulse height analyzer were LL=1V and UL=3V, respectively, is shown in FIG. 4. In this FIG. 4, the dead time with Cu—Kα line is taken as a reference value of 0 and the dead times with other fluorescent X-rays are plotted in terms of the difference from the reference value. As shown in FIG. 4, it has been ascertained that there is a linear correlation between the energy resolution of the detector and the dead time.

In view of the foregoing, arrangement has been made that while the proportionality coefficient of the energy resolution of the detector 7 relative to the inverse of the square root of the energy of the fluorescent X-rays 6 and the correlation between the energy resolution of the detector 7 and the dead time are stored beforehand in the counting loss correcting unit 11, the dead time may be determined so as to correspond to the energy of the fluorescent X-rays during the measurement on the basis of the stored proportionality coefficient and the stored correlation. More specifically, this correlation is a table drawn up by determining the rate of change (gradient) of the dead time relative to the energy resolution of the detector 7 for each of the representative combinations of the preset lower and upper limit values of the pulse height analyzer 9. Even in this case, in a plurality of the spectrometers of the same kind, in which the sake kinds of detectors and counting units (counting circuits) are used, it is necessary for the proportionality coefficient to be determined and stored in such spectrometer, but as far as the correlations are concerned, it is recommended to store the correlation already determined in the standard spectrometer, which is of the same kind as such spectrometer.

Summarizing the foregoing, it will readily seen that the counting loss correcting unit 11 employed in this spectrometer determines the dead time in accordance with the following equation (4) below.

$$\tau=\tau^{PHA}(LL,UL)\cdot\tau i/\tau b+\Delta\tau^E(LL,UL) \quad (4)$$

In the equation (4) above, $\tau$ represents the dead time so determined; $\tau^{PHA}(LL, UL)$ represents the dead time in the standard spectrometer at the predetermined pulse height range (a combination of the preset lower and upper limit values of the pulse height analyzer) during the measurement, which is determined directly or through a linear interpolation from the previously described correlation between the predetermined pulse height range and the dead time in the standard spectrometer, that is, the table; τi represents the dead time in such spectrometer at the predetermined pulse height range used as a basis; and τb represents the dead time in the standard spectrometer at the predetermined pulse height range used as a basis.

The term, $\Delta\tau^E$(LL, UL), represents an amount of adjustment of the dead time corresponding to the energy of the fluorescent X-rays during the measurement and is determined in the following manner on the basis of the proportionality coefficient and the correlation both stored in the manner described previously. At the outset, from the proportionality coefficient k of the energy resolution of the detector relative to the inverse of the square root of the energy E of the fluorescent X-rays, which has been determined with respect to such spectrometer and subsequently stored, the energy resolution with respect to the energy Ex of the fluorescent X-rays during the measurement can be determined as $k/(Ex)^{1/2}$, and the energy resolution with respect to the energy Eo of the fluorescent X-rays, which energy Eo provides a basis, can be determined as $k/(Eo)^{1/2}$. Also, from the correction between the energy resolution of the detector and the dead time, that is, from the table drawn up by determining the rate of change (gradient) of the dead time relative to the energy resolution of the detector for each of the representative combinations of the preset lower and upper limit values of the pulse height analyzer in the standard spectrometer, the rate of change K in the predetermined pulse height range (the combination of the preset lower and upper limit values of the pulse height analyzer) during the measurement can be determined directly or through linear interpolation. From these, the term, $\Delta\tau^E$(LL, UL), can be determined according to the equation (5) below.

$$\Delta\tau^E(LL,UL)=K(k/(Ex)^{1/2}-k/(Eo)^{1/2}) \qquad (5)$$

With respect to the correction error of the counting loss correction, comparisons between numerical values exhibited by the spectrometer according to the first embodiment of the present invention and numerical values exhibited by the conventional spectrometer are tabulated in the following table 1 below.

TABLE 1

| Measured Rays | LL (V) | UL (V) | Correction Error (%) in Invention | Correction Error (%) in Conventional |
|---|---|---|---|---|
| Cu-KA | 1.0 | 2.5 | 0.5 | 5.8 |
| Cr-KA | 1.3 | 2.7 | 0.6 | 6.1 |
| Ti-KA | 1.0 | 5.0 | 0.4 | 13.2 |

From the table 1 above, it is clear that according to the spectrometer designed in accordance with the first embodiment of the present invention, first of all, the counting rate of the pulses determined by the counting unit can be accurately corrected even though the predetermined pulse height range set in the pulse height analyzer is changed. Here, there is no need to determine beforehand the correlation between the predetermined pulse height range and the dead time in such spectrometer and the correlation between the predetermined pulse height range and the dead time, determined by the standard spectrometer, which is of the same kind as such spectrometer, can be utilized. It is also clear that according to the spectrometer designed in accordance with the first embodiment of the present invention, even when not only the predetermined pulse height range set in the pulse height analyzer, but also the energy of the fluorescent X-rays incident on the detector change, the counting rate of the pulses determined by the counting unit can be accurately corrected.

It is to be noted that since in a spectrometer such as, for example, a simultaneous multi-element analysis type X-ray fluorescence spectrometer, which is equipped with fixed channels employing a spectroscopic device and a detector for each of elements to be measured, the energy of the fluorescent X-rays to be measured at each of those channels do not change, the adjustment of the dead time for corresponding to the energy of the fluorescent X-rays during the measurement, that is, the term of $\Delta\tau^E$(LL, UL) in the equation (4) above is unnecessary.

The wavelength dispersive X-ray fluorescence spectrometer according to a second preferred embodiment of the present invention will be now described. The spectrometer according to the second embodiment, when compared with the previously described spectrometer according to the first embodiment, differs in only the manner of determining the dead time so as to corresponding to the predetermined pulse height range during the measurement, which is performed by the counting loss correcting unit, and in the spectrometer according to the second embodiment, the counting loss correcting unit 12 stores beforehand a plurality of pulse height distributions for their respective counting rates (a plurality of pulse height distributions, in which the sums of counting rates of the entire pulse height distribution are different from each other) and, on the basis of the stored pulse height distributions, the dead time is determined so as to correspond to the predetermined pulse height range during the measurement. More specifically, the dead time is determined in the following manner.

At the outset, the measurement is carried out using a standard sample to obtain a first pulse height distribution at the tube current value of, for example, 5 mA and a second pulse height distribution at the tube current value of, for example, 50 mA, which distributions are then stored beforehand in the counting loss correcting unit 12. Those pulse height distributions may be determined by means of a multichannel pulse height analyzer or, alternatively, using a single channel pulse height analyzer by incrementally increasing the preset lower limit value LL while the window size between the preset lower limit value LL and the preset upper limit value UL is maintained fixed and narrow.

The counting loss correcting unit 12 determines a counting rate $Nm_{B1}$ at the tube current value of 5 mA from the first pulse height distribution and a counting rate $Nm_{B2}$ at the tube current value of 50 mA from the second pulse height distribution with respect to the predetermined pulse height range during the measurement of the sample to be analyzed (which is the pulse height range that is included not only in the first pulse height distribution, but also in the second pulse height distribution and which is referred to as the pulse height range B). Since if the counting rate $Nm_{B1}$, when the counting loss thereof is accurately corrected, becomes counting rate $Nt_{B1}$, and the counting rate $Nm_{B2}$, when the counting loss thereof is accurately corrected, ought to become counting rate $10Nt_{B1}$, and if dead time for the pulse height range B is expressed by $\tau_B$, equations similar to the previously discussed equations (2) and (3) are established and it can be determined by calculating the dead time $\tau_B$ for the pulse height range B.

Even with the spectrometer according to the second embodiment of the present invention, in a manner similar to the spectrometer according to the previously described first embodiment, the counting rate determined by the counting unit can be accurately corrected even though the predetermined pulse height range set in the pulse height analyzer is changed. Also, even in the spectrometer according to the above described second embodiment, in a manner similar to the previously described first embodiment, the dead time is preferably determined additionally so as to correspond to the energy of the fluorescent X-rays during the measurement if so required.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

| [Reference Numerals] | |
| --- | --- |
| 1 | X-ray source |
| 2 | Primary X-rays |
| 3 | Sample |
| 4 | Fluorescent X-rays emitted from the sample |
| 5 | Spectroscopic device |
| 6 | Fluorescent X-rays monochromated by the spectroscopic device |
| 7 | Detector |
| 9 | Pulse height analyzer |
| 10 | Counting unit |
| 11, 12 | Counting loss correcting unit |

What is claimed is:

1. A wavelength dispersive X-ray fluorescence spectrometer which comprises:
    an X-ray source for irradiating a sample with primary X-rays;
    a spectroscopic device for monochromating fluorescent X-rays emitted from the sample;
    a detector for receiving the fluorescent X-rays, which have been monochromated by the spectroscopic device, and generating pulses of a pulse height proportional to an energy of the fluorescent X-rays in a number dependent on an intensity of the fluorescent X-rays;
    a pulse height analyzer for selecting pulses of a pulse height within a predetermined pulse height range from the pulses generated by the detector;
    a counting unit for determining a counting rate of the pulses selected by the pulse height analyzer; and
    a counting loss correcting unit for correcting the counting rate of the pulses, determined by the counting unit, on the basis of a dead time of the detector with respect to a counting loss of the pulses to be counted;
    the counting loss correcting unit stores beforehand a correlation between each of a plurality of representative predetermined pulse height ranges and the dead time, and determines the dead time, which corresponds to the predetermined pulse height range during a measurement, on the basis of the correlation so stored,
    wherein the counting loss correcting unit stores beforehand a correlation between each of a plurality of representative predetermined pulse height ranges and the dead time in a standard spectrometer to be used as a basis, which is of the same kind as such wavelength dispersive X-ray fluorescence spectrometer, and a ratio between the dead time in such wavelength dispersive X-ray fluorescence spectrometer and the dead time in the standard spectrometer for a predetermined pulse height range to be used as a basis and determines the dead time, which corresponds to the predetermined pulse height range during the measurement, on the basis of the correlation and the ratio so stored.

2. The wavelength dispersive X-ray fluorescence spectrometer as claimed in claim 1, in which the counting loss correcting unit further stores beforehand a proportionality coefficient of an energy resolution of the detector relative to the inverse of the square root of the energy of the fluorescent X-rays and a correlation between the energy resolution of the detector and the dead time and determines the dead time, which corresponds to the predetermined pulse height range during the measurement, on the basis of the proportionality coefficient and the correlation so stored.

3. A wavelength dispersive X-ray fluorescence spectrometer which comprises:
    an X-ray source for irradiating a sample with primary X-rays;
    a spectroscopic device for monochromating fluorescent X-rays emitted from the sample;
    a detector for receiving the fluorescent X-rays, which have been monochromated by the spectroscopic device, and generating pulses of a pulse height proportional to an energy of the fluorescent X-rays in a number dependent on an intensity of the fluorescent X-rays;
    a pulse height analyzer for selecting pulses of a pulse height within a predetermined pulse height range from the pulses generated by the detector;
    a counting unit for determining a counting rate of the pulses selected by the pulse height analyzer; and
    a counting loss correcting unit for correcting the counting rate of the pulses, determined by the counting unit, on the basis of a dead time of the detector with respect to a counting loss of the pulses to be counted;
    the counting loss correcting unit stores beforehand a plurality of pulse height distributions for their respective counting rates and determines the dead time, which corresponds to the predetermined pulse height range during a measurement, on the basis of the plurality of pulse height distributions and the counting rates so stored.

4. The wavelength dispersive X-ray fluorescence spectrometer as claimed in claim 3, in which the counting loss correcting unit further stores beforehand a proportionality coefficient of an energy resolution of the detector relative to the inverse of the square root of the energy of the fluorescent X-rays and a correlation between the energy resolution of the detector and the dead time and determines the dead time, which corresponds to the predetermined pulse height range during the measurement, on the basis of the proportionality coefficient and the correlation so stored.

* * * * *